United States Patent [19]

Kubota et al.

[11] Patent Number: 4,771,084

[45] Date of Patent: Sep. 13, 1988

[54] LIGHT CURING COMPOSITIONS FOR DENTAL RESTORATION

[75] Inventors: Takao Kubota, Kamakura; Tetsuro Sakuma; Ryoji Nakazato, both of Tokorozawa, all of Japan

[73] Assignee: G-C Dental Industrial Corp., Tokyo, Japan

[21] Appl. No.: 906,285

[22] Filed: Sep. 11, 1986

[30] Foreign Application Priority Data

Sep. 11, 1985 [JP] Japan ............................... 60-199387

[51] Int. Cl.$^4$ ........................... C08F 2/50; C08F 4/40; C08L 63/10; C08K 9/06
[52] U.S. Cl. .......................................... 522/10; 522/8; 522/14; 522/77; 522/28; 522/96; 522/103; 522/908; 523/116
[58] Field of Search ..................................... 522/10, 8

[56] References Cited

U.S. PATENT DOCUMENTS

| | | | |
|---|---|---|---|
| 3,801,329 | 4/1974 | Sandner | 522/8 |
| 3,992,275 | 11/1976 | Shahidi | 522/8 |
| 4,040,925 | 8/1977 | McGinniss | 522/33 |
| 4,269,931 | 5/1981 | Suzuki | 522/18 |
| 4,271,258 | 6/1981 | Watariguchi | 522/8 |
| 4,411,625 | 10/1983 | Koblitz | 522/10 |

FOREIGN PATENT DOCUMENTS 1177301 11/1984 Canada .
1575873 10/1980 United Kingdom .

*Primary Examiner*—John C. Bleutge
*Assistant Examiner*—A. H. Koeckert
*Attorney, Agent, or Firm*—Oblon, Fisher, Spivak, McClelland & Maier

[57] ABSTRACT

A novel light curing composition for dental restoration comprises (a) a polymerizable compound containing at least one ethylenically unsaturated double-bond, (b) at least one photo-polymerization initiator selected from ketal base compounds defined hereinafter, (c) at least one photo-polymerization initiator selected from benzoin alkyl ether base compounds defined hereinafter, (d) a reducing agent and (e) a filler.

5 Claims, No Drawings

LIGHT CURING COMPOSITIONS FOR DENTAL RESTORATION

BACKGROUND OF THE INVENTION

1. Field of the Invention

The present invention relates to a light curing composition for dental restoration and, more particularly, to a light curing composition for dental restoration which shows high sensitivity with respect to light sources for emitting both visible light and ultraviolet light, and provides a polymerization-cured mass excelling in color stability and physical properties.

2. State of the Prior Art

As well-known in the art, the so-called chemical curing type and light curing type of dental composite resins for restoration are used in dentistry to which the invention belongs. The chemical curing type of composite resins for filling are a pasty product composed mainly of a finely divided inorganic filler and a binder resin for bonding together filler particles. This pasty product is divided into two portions, one portion containing a peroxide and the other portion containing an amine. For use, these pasty portions are mixed together, and the resulting mixture is filled in a dental caries cavity. Thereafter, the binder-resin are polymerized and cured by the peroxide-amine redox reaction within a certain period of time. In view of manipulation, this type of resin has a disadvantage that its curing time is so certain that an operator should finish filling work while the paste still maintains its plasticity prior to curing.

With reference to the light curing type of composite resins for filling which makes use of a photo-polymerization catalyst in place of the peroxide-amine base catalyst used for chemical polymerization, the curing reaction does not proceed, unless they are exposed to light. For that reason, they have a number of advantages that their mainipulation and curing time are substantially controlled depending upon an operator's will so as to obtain the optimum results in respect of the treatment procedure and time to be applied. In dentistry, the light curing type of filling materials now enjoy increasing use.

Out of a number of compositions for the light curing type dental filling materials known in the art, there are often used visible light curing type of filling materials in view of the fact that they can harmlessly be used in the oral mouth, in particular. For instance, such compositions are disclosed in British Pat. No. 1,408,265 as well as Japanese Patent Laid-Open Nos. 57-187377, 53-62394, 57-54107, 57-77609 and 58-65704, which are associated with the use of an alpha-diketone and a reducing agent, as disclosed in British Pat. No. 1,408,265 specification. In most cases, however, actually available products make use of camphor quinone.amine combinations.

The visible light curing type of filling materials cure in a wavelength region of 400–500 nm, but do not provide any satisfactory cured mass in a wavelength region of below 400 nm. They are also adversely affected by the intensity of light, so that insufficient reactions tend to take place in a portion away from a light-emitting source, leaving a larger amount of the residual monomer behind. This often results in deteriorations in the color stability and physical properties from the clinical point-of-view.

Ultraviolet light curing type of dental compositions are known from Japanese Patent Kokoku-Publication No. 51-2235 and Japanese Patent Laid-Open No. 53-82088, for instance. Ultraviolet light having a wavelength of 300 nm or lower cannot directly be used in the oral mouth, since they are harmful to the human body. As pointed out previously, their defect is a limited curing depth.

The aforesaid two types of filling compositions are designed to cure in their exclusive wavelength regions. Thus, any light curing type of polymerizable compositions are not still known in the art, which are capable of curing well in both ultraviolet and visible light regions.

SUMMARY OF THE INVENTION

It is, therefore, an object of the present invention to provide a light curing composition for dental restoration of high sensitivity.

According to the present invention, it has been found that the coexistence of three constitutional components, i.e., two photo-polymerization initiators, a ketal base compound and a benzoin alkyl ether base compound, and a reducing agent produces a photo-polymerization initiation capability in both ultraviolet and visible light regions due to their synergistic effect.

Use of the ketal base compound alone or in combination with the reducing agent is effective for ultraviolet light of below 400 nm, but is substantially ineffective for visible light of 400 nm or higher in view of the photo-polymerization initiation capability. On the other hand, use of the benzoin alkyl ether compound alone or in combination with the reducing agent produces little or no photo-polymerization initiation capability for visible light of 400 nm or higher and any satisfactory cured mass is not obtained. Compositions comprising a mixture system of the ketal and benzoin alkyl ether base photo-polymerization initiators and not relying upon any reducing agent are found to show a slight photo-polymerization property, but their cured mass has insufficient strength and is practically of useless, when used as the dental restorative materials.

It has now been found that the compositions of the present invention comprising a combination of a ketal base compound, a benzoin alkyl ether base compound and a reducing agent show preferred properties in dentistry, since they excel especially in the polymerization initiation capability for light of 300–500 nm and their mass excels in strength and hardness, and do also exhibit improved color stability which is an important factor in dentistry.

More specifically, the present invention provides a light curing composition for dental restoration characterized by comprising the following five constitutional components:

(a) a polymerizable compound containing at least one ethylenically unsaturated double-bond, (b) at least one photo-polymerization initiator selected from ketal base compounds expressed in terms of the following general formula [1]:

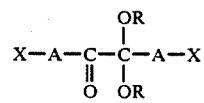

[1]

wherein
X is H, Cl, an alkyl group having 1 to 5 carbon atoms or an alkoxy group having 1 to 5 carbon atoms,
A is a six-membered aromatic group, and R is an alkyl group having 1 to 10 carbon atoms, an aralkyl group having 7 to 9 carbon atoms or a $\text{-(}C_nH_{2n}O\text{)}_{\overline{m}}R'$ in which n is an integer of 2 to 5, m is an integer of 1 to 5 and R' is an alkyl group having 1 to 5 carbon atoms, (c) at least one photo-polymerization initiator selected from benzoin alkyl ether base compounds expressed in terms of the following general formula [2]:

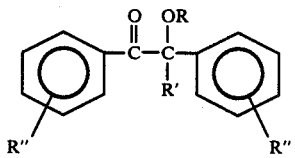

wherein
R is an alkyl group,
R' is selected from the group consisting of a hydrogen atom, an alkyl group, a halogen atom and an alkoxy group, and
R" is one or more groups which may optionally be present on the respective phenyl rings of that formula, and are selected from the group consisting of an alkyl group, an alkoxy group, a halogen atome and an alkylamino group, (d) a reducing agent, and
(e) a filler.

The first constitutional component in the compositions of the present invention, i.e., the ethylenical compounds refer to those having in their chemical structure at least one ethylenically unsaturated double-bond, and taking on the chemical form of monomers, prepolymers (viz., dimers, trimers and other oligomers) or mixtures and copolymers thereof.

Concretely speaking, the monomers having therein one ethylenically unsaturated double-bond include methyl, ethyl, isopropyl, hydroxyethyl, tetrahydrofurfuryl and glycidyl methacrylates, and acrylates thereof, and the monomers having therein two ethylenically unsaturated double-bonds include 2,2-bis(methacryloxyphenyl)propane, 2,2-bis[4-(2-hydroxy-3-methacryloxyphenyl)]propane, 2,2-bis(4-methacryloxyethoxyphenyl)propane, 2,2-bis(4-methacryloxydiethoxyphenyl)propane, 2,2-bis(4-methacryloxypropoxyphenyl)propane and acrylates thereof. The aliphatic monomers include ethylene glycol, diethylene glycol, triethylene glycol, butylene glycol, neopentyl glycol, 1,3-butanediol, 1,4-butanediol and 1,6-hexanediol dimethacrylates and acrylates thereof. The monomers having therein three ethylenically unsaturated double-bonds include trimethylolpropane, trimethylolethane, pentaerythritol and trimethylolmetane trimethacrylates and acrylates thereof. The monomers having therein four ethylenically unsaturated double-bonds include pentaerythritol tetramethacrylate and tetracrylate as well as the urethane base monomers expressed in terms of the following structural formulae (3) and (4):

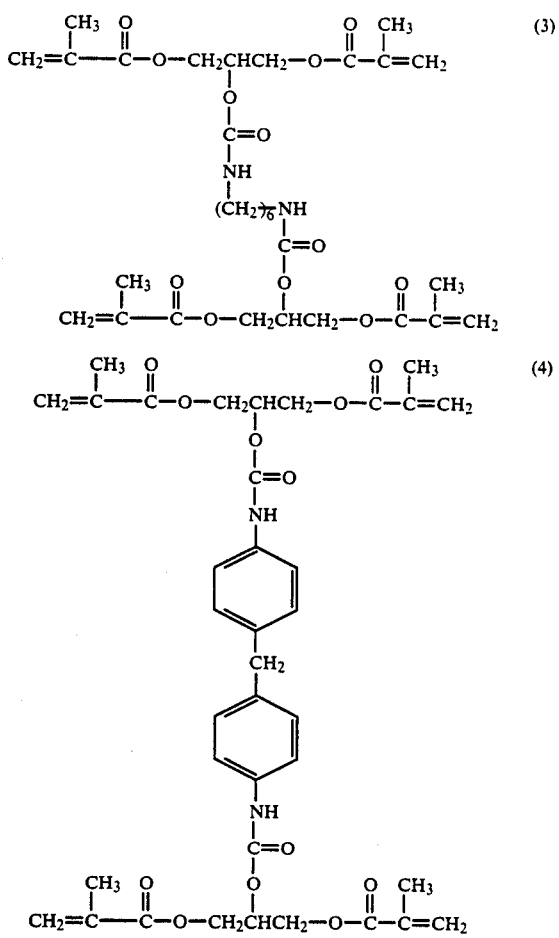

Other monomers include 4-methacryloxyethyl trimellitic acid and its anhydrides. These acrylates and methacryates may be used alone or in combination.

Preferably, these compounds having an ethylenically unsaturated double-bond or bonds should be used in an amount of 90-10 weight % with respect to the filler. When the amount of the compounds having an ethylenically unsaturated double-bond or bonds departs from the aforesaid range, any satisfactory filling material is not formed.

The ketal base compounds used as the second constitutional component and expressed in terms of the general formula [1] include, in addition to benzil dimethyl ketal having the following formula:

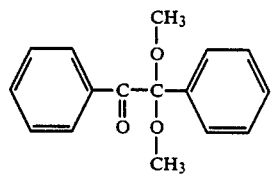

benzil diethyl ketal, benzil dipropyl ketal, benzil-di(-betaphenylethyl)ketal, benzil-di(2-methoxyethyl)ketal, benzil-di(2-ethoxyethyl)ketal, benzil-di(2-methoxyethoxyethyl)ketal, benzil-di(2-ethoxyethoxyethyl)ketal, 4,4'-dimethylbenzil-dimethyl ketal, 2,2'-dimethoxybenzil-diethyl ketal, 4,4'-dichlorobenzil-diethyl ketal, 4,4'-dichlorobenzil-dipropyl ketal and so on. Among others, particular preference is given to benzil dimethyl ketal, benzil diethyl ketal, benzil-di(2-methoxyethyl)ketal and 4,4'-dimethylbenzil-dimethyl ketal.

The benzoin alkyl ether base compounds used as the third constitutional component in the present invention include benzoin methyl ether, benzoin ethyl ether, benzoin isopropyl ether, benzoin-n-butyl ether and benzoin isobutyl ether and so on. Among others, particular preference is given to benzoin isobutyl ether. These photopolymerization initiators may be used alone or in admixtures of two or more thereof.

Referring to the amounts of the aforesaid ketal and benzoin alkyl ether base photo-polymerization initiators added, it is preferred that they be added in an amount of 0.01 to 5% weight relative to the compound having an ethylenically unsaturated double-bond or bonds. In ranges departing from that as mentioned just above, the resulting curing property and color stability are practically unsuitable for use in dentistry.

As the reducing agents that are the fourth constitutional component in the present invention, use is made of compounds which are capable of reducing photosensitizers, when they are excited, but are incapable of reducing them, when they are not excited by active energy beams. The reducing agents may be primary, secondary or tertiary amines. In the amine

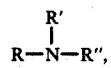

none of R, R' and R" may be a hydrogen atom, or one or two of R, R' and R" may be a hydrogen atom. One or more groups of R, R' and R" may be different or identical hydrocarbon groups, which may be alkyl, cycloalkyl, hydroxyalkyl or aralkyl groups, for instance. Preferred R, R' and R" groups are $C_1$–$C_{10}$ alkyl groups.

Suitable examples of the reducing agents, wherein one or more units represented by R, R' and R" are hydrocarbons, include propylamine, n-butylamine, pentylamine, hexylamine, dimethylamine, diethylamine, dipropylamine, di-n-butylamine, dipentylamine, trimetylamine, triethylamine, tripropylamine, tri-n-butylamine, tripentylamine, dimethylaminoethyl methacrylate, diethylaminoethyl methacrylate, triethanolamine, dimethylaminoethanol and long-chain aliphatic amines.

Examples of the reducing agents containing an aromatic group include N,N'-dimethylaniline, N-methyldiphenylamine, 2-dimethylaminobenzoic acid ethyl ester, 4-dimethylaminobenzoic acid ethyl ester, 4-dimethylaminobenzoic acid methyl ester, 4-dimethylaminobenzoic acid butyl ester, 4-dimethylaminobenzoic acid 2-ethylhexyl ester and 4-dimethylaminobenzoic acid isoamyl ester.

Use may be made of a diamine having the structure of

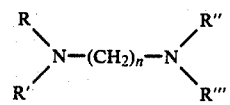

wherein n is an integer of 2 or higher, and different or identical groups R, R', R" and R''' are a hydrogen atom or hydrocarbon groups, particularly alkyl groups. The type of reducing agent may be exemplified by ethylenediamine, trimethylenediamine, tetramethylenediamine, pentamethylenediamine or hexamethylenediamine or N-hydrocarbon derivatives, especially N-alkyl derivatives.

Examples of the reducing agents in which an element N forms a part of ring include, for instance, piperidine and N-hydrocarbon derivatives thereof.

Other reducing agents which may be used in the present invention include triaryl amines, allyl thiourea, aromatic sulfinates, 5-alkyl or 5-aryl-barbituric acid and so on.

Among these reducing agents, preference is given to dimethylaminoethyl methacrylate, triethanolamine, 4-dimethylaminobenzoic acid methyl ester and 4-methylaminobenzoic acid ethyl ester.

The concentration of these reducing agents is preferably 0.01 to 5 weight % based on the ethylenically unsaturated substance in view of dental color stability and curing property.

In addition to the aforesaid constitutional components, if required, the compositions of the present invention may contain polymerization inhibitors, ultraviolet absorbers and organic peroxides which are usually used.

The fifth constitutional filler component may be inorgaic and/or organic fillers. Suitable examples of fillers include inorganic fillers such as quartz, alumima, glass, kaolin, talc, calcium carbonate, barium aluminosilicate glass, titanium oxide, borosilicate glass, and colloidal silica and the so-called organic composite filler in which an inorganic filler is coated with an organic polymer and organic fillers such as polymethyl acrylate, polymethyl methacrylate, polyethyl methacrylate, copolymers of methyl methacrylate with ethyl methacrylate, crosslinked type polymethyl methacrylate and copolymers of ethylene with vinyl acetate. These polymer powders may be used in the form of mixtures with the aforesaid inorganic powders.

It is preferred that, prior to mixing the inorganic filler with the binder resin, that filler is treated on its surface with a coupling agent capable of reacting with both the filler and the binder resin. The coupling agents used may include a silane coupling agent, a titanate coupling agent, an aluminate coupling agent an so on. Alternatively, the inorganic filler may be grafted on the surface for bonding to the binder resin.

The silane coupling agents used to this end include γ-methacryloxypropyl trimethoxysilane, vinyltrichlorosilane, vinyl-tris(β-methoxyethoxy)silane, γ-methacryloxypropylmethyl dimethoxysilane, γ-glycidoxypropyl trimethoxysilane, γ-chloropropyltrimethoxysilane, β-(3,4-epoxycyclohexyl)ethyl trimethoxysilane, trimethylchlorosilane, dimethyldichlorosilane, hexamethyldisilane, γ-amiooropyl triethoxysilane, N-β-(aminoethoxy)-γ-aminopropyl trimethoxysilane, γ-urenoidopropyl trimethoxysilane and so on.

In the present invention, any method for surface treatment with these coupling agents may be used. The amount of said surface treatment agents used varies depending upon the nature and state required, and is not generally determined. Generally, however, said surface treatment agents may be used in an amount ranging from 0.1 to 20 weight %, preferably 1 to 10 weight % relative to the inorganic matter.

The active energy beams used in the present invention may be visible light or ultraviolet light, or may contain their spectra both visible and ultraviolet light. A preferred wavelength ranges from 240 nm to 600 nm. The light sources applicable to the compositions of the present invention include carbon arc, mercury lamps, xenon lamps, metal halide lamps, fluoroescent lamps, tungsten lamps and argon ion laser.

The present invention will now be explained in further detail with reference to the following non-restrictive examples and comparison examples.

EXAMPLE 1

Seventy (70) grams of 2,2-bis[4- (2-hydroxy-3-methacryloxyphenyl)]propane, 30 grams of triethylene glycol dimethacrylate, 0.5 grams of benzil dimethyl ketal, 0.5 grams of benzoin isobutyl ether and 0.5 grams of dimethylaminoethyl methacrylate were roll-mixed at room temperature with 100 grams of finely divided silica treated on the surface with 3 grams of γ-methacryloxypropyl trimethoxysilane to prepare a composition. The paste was then filled in a Teflon plate formed therein with a round hole having a diameter of 3 mm and a thickness of 3 mm, and the assembly was exposed, from 1 mm above, to visible light (Trade Name: Luxor made by ICI) to determine the color stability and compressive strength of the cured mass. Examination was made of the rate of penetration of a 1 kg-loaded kneedle into the surface of the test plate opposite to that thereof to be exposed to visible light to express the curing time in terms of the shortest visible light-exposing time in which the rate of penetration assumed zero. In the tables to be given below, the bracketed figures are the curing time measured with ultraviolet light (Trade Name: Permacure-UC-1 made by GC) in the same manner. A stainless steel mold was also provided therethrough with a round hole of 4 mm in diameter and 10 mm in thickness, in which said paste was filled, followed by covering the surface thereof with a cellophane paper. Thereafter, the assembly was exposed to visible light (Trade Name: Luxor made by ICI) for 45 seconds. The polymer was then taken out of the round hole to remove unreacted matters, and was measured in respect of its length for curing depth. The results are set forth in the tables.

EXAMPLES 2–7 AND COMPARISON EXAMPLES 1 TO 10

In accordane with Example 1, examinations were made of the curing time, color stability, compressive strength and curing depth of various compositions, wherein the ketal base compounds, benzoin alkyl ether base compounds and reducing agents set forth in the tables were used in the amounts specified therein in place of those described in Example 1. In Comparison Examples 1, 2 and 3, experiments were each carried out without using the ketal base compound, benzoin alkyl ether base compound and reducing agent, respectively. In Comparison Example 10, use was made of camphor quinone which enjoys wide use as commercially available products. The results are summarized in the tables.

EXAMPLES 8 AND 9

In accordance with Example 1, examinations were made of the curing time, color stability, compressive strength and curing depth of various compositions, wherein 70 grams of an aliphatic urethane dimethacrylate and 30 grams of butanediol dimethacrylate were used as the monomer components in the composition of Example 1, and the ketal and benzoin alkyl ether base compounds and reducing agent set forth in the tables were used in the amounts specified therein. The results are summarized in the tables.

|  | Example 1 | Example 2 | Example 3 | Example 4 | Example 5 |
|---|---|---|---|---|---|
| Ketal Base Compound | benzil Dimethyl Ketal | benzil Dimethyl Ketal | benzil Dimethyl Ketal | benzil Dimethyl Ketal | benzil Dimethyl Ketal |
| Amount (g) | 0.5 | 0.5 | 0.5 | 0.5 | 0.5 |
| Benzoin Alkyl Ether Base Compound | Benzoin Isobutyl Ether | Benzoin Isobutyl Ether | Benzoin Isobutyl Ether | Benzoin Isobutyl Ether | Benzoin Isobutyl Ether |
| Amount (g) | 0.5 | 0.5 | 0.5 | 0.5 | 0.5 |
| Reducing Agent | Dimethylaminoethyl-methacrylate | Triethanolamine | 4-Dimethylamino-benzoic Acid Ethyl Ester | 4-Dimethylamino-benzoic Acid Ethyl Ester | 4-Dimethylamino-benzoic Acid Ethyl Ester |
| Amount (g) | 0.5 | 0.5 | 0.5 | 0.5 | 0.5 |
| Curing Time Visible Light (min. sec.) | 30″ | 30″ | 30″ | 35″ | 35″ |
| Ultraviolet Light (min. sec.) | (1′20″) | (1′20″) | (1′25″) | (1′30″) | (1′35″) |
| Compressive Strength (kg/cm$^2$) | 3871 | 3721 | 3792 | 3520 | 3488 |
| Curing Depth (mm) | 4.61 | 4.72 | 4.85 | 4.39 | 4.20 |
| Color Stability | Colorless | Colorless | Colorless | Colorless | Colorless |

|  | Example 6 | Example 7 | Example 8 | Example 9 | | Comparative Example 1 |
|---|---|---|---|---|---|---|
| Ketal Base Compound | benzil-di(2-Methoxyethyl) Ketal | 4,4′-dimethylbenzil-dimethyl Ketal | Benzil Dimethyl Ketal | Benzil Dimethyl Ketal | Benzil Dimethyl Ketal | Benzil Dimethyl Ketal |
| Amount (g) | 0.5 | 0.5 | 0.5 | 0.25 | 0.25 | 0.5 |
| Benzoin Alkyl Ether Base Compound | Benzoin Isobutyl Ether | Benzoin Isobutyl Ether | Benzoin Isobutyl Ether | Benzoin Isobutyl Ether | | — |
| Amount (g) | 0.5 | 0.5 | 0.5 | 0.5 | | |
| Reducing Agent | 4-Dimethylamino-benzoic Acid Ethyl Ester | 4-Dimethylamino-benzoic Acid Ethyl Ester | 4-Dimethylamino-benzoic Acid Ethyl Ester | 4-Dimethylamino-benzoic Acid Ethyl Ester | | Dimethylaminoethyl-methacrylate |
| Amount (g) | 0.5 | 0.5 | 0.5 | 0.5 | | 0.5 |

-continued

| Curing Time | | | | | |
|---|---|---|---|---|---|
| Visible Light (min. sec.) | 35" | 35" | 25" | 25" | Not cured |
| Ultraviolet Light (min. sec.) | (1'35") | (1'40") | (1'15") | (1'15") | (1'50") |
| Compressive Strength (kg/cm$^2$) | 3375 | 3298 | 3917 | 3890 | — |
| Curing Depth (mm) | 4.11 | 4.33 | 5.39 | 5.44 | — |
| Color Stability | Colorless | Colorless | Colorless | Colorless | — |

| | Comparative Example 2 | Comparative Example 3 | Comparative Example 4 | Comparative Example 5 | Comparative Example 6 |
|---|---|---|---|---|---|
| Ketal Base Compound | — | Benzil Dimethyl Ketal | Benzil Dimethyl Ketal | Benzil Dimethyl Ketal | Benzil Dimethyl Ketal |
| Amount (g) | | 0.5 | 0.005 | 6 | 0.5 |
| Benzoin Alkyl Ether Base Compound | Benzoin Isobutyl Ether | Benzoin Isobutyl Ether | Benzoin Isobutyl Ether | Benzoin Isobutyl Ether | Benzoin Isobutyl Ether |
| Amount (g) | 0.5 | 0.5 | 0.5 | 0.5 | 0.005 |
| Reducing Agent | Dimethylaminoethyl-methacrylate | — | 4-Dimethylamino-benzoic Acid Ethyl Ester | 4-Dimethylamino-benzoic Acid Ethyl Ester | 4-Dimethylamino-benzoic Acid Ethyl Ester |
| Amount (g) | 0.5 | | 0.5 | 0.5 | 0.5 |
| Curing Time | | | | | |
| Visible Light (min. sec.) | >2'00" | 2'00" | >2'00" | 30" | Not cured |
| Ultraviolet Light (min. sec.) | (6'00") | (4'30") | (6'00") | (1'20") | (1'50") |
| Compressive Strength (kg/cm$^2$) | — | — | — | 1379 | — |
| Curing Depth (mm) | — | — | — | 4.88 | — |
| Color Stability | — | — | — | Colorless | — |

| | Comparative Example 7 | Comparative Example 8 | Comparative Example 9 | Comparative Example 10 |
|---|---|---|---|---|
| Ketal Base Compound | Benzil Dimethyl Ketal | Benzil Dimethyl Ketal | Benzil Dimethyl Ketal | Camphorquinone |
| Amount (g) | 0.5 | 0.5 | 0.5 | 0.5 |
| Benzoin Alkyl Ether Base compound | Benzoin Isobutyl Ether | Benzoin Isobutyl Ether | Benzoin Isobutyl Ether | — |
| Amount (g) | 6 | 0.5 | 0.5 | |
| Reducing Agent | 4-Dimethylamino-benzoic Acid Ethyl Ester | 4-Dimethylamino-benzoic Acid Ethyl Ester | 4-Dimethylamino-benzoic Acid Ethyl Ester | Hexylamine |
| Amount (g) | 0.5 | 0.005 | 6 | 0.5 |
| Curing Time | | | | |
| Visible Light (min. sec.) | 30" | 2'00" | 30" | 45" |
| Ultraviolet Light (min. sec.) | (1'20") | (4'30") | (1'20") | Not cured |
| Compressive Strength (kg/cm$^2$) | 1722 | — | 3288 | 3401 |
| Curing Depth (mm) | 4.38 | — | 4.76 | 3.08 |
| Color Stability | Colorless | — | Yellow | Yellow |

As appreciated from the results of Examples 1 to 9, the compositions according to the present invention show more improved curing property with respect to the light source for both visible light and ultraviolet light over the prior art composition (Comparison Example 10), and are found to be cured by short-period irradiation and have a large curing depth. Furthermore, the cured masses obtained from the invented compositions show no sign of coloring and are substantially colorless, and thus have more improved color stability over the prior art cured mass (Comparison Example 10). The cured masses according to the present invention have also high strength.

The light curing compositions for dental restoration according to the present invention provide cured masses having improved physical properties by light irradiation in a short period of time, even though the filling material is large in thickness.

With the restorative materials obtained from the compositions of the present invention, clinically satisfactory results are obtained even after the lapse of two years in the oral mouth. In other words, they substantially show no sign of discoloration, wearing and breaking, unlike the conventional products. Thus, the restorative materials obtained from the compositions according to the present invention can satisafctorily be used for the dental purposes including dental composite resins for filling, synthetic resins for crown, resins for inlay, resins for jacket crown, resin teeth, acrylic denture base resins, repaired resins, acrylic resins for denture rebase, resins for impression tray and orthodontic resins.

What is claimed is:

1. A light curing paste composition for dental restoration comprising the following five constitutional components:
   (a) a polymerizable compound containing at least one ethylenically unsaturated double-bond;
   a photo-polymerization initiator system consisting essentially of:
   (b) at least one photo-polymerization initiator selected from ketal base compounds expressed in terms of the following general formula (1):

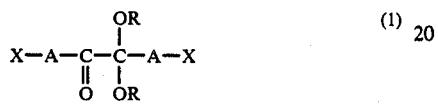

wherein
   X is H, Cl, an alkyl group having 1 to 5 carbon atoms or an alkoxy group having 1 to 5 carbon atoms,
   A is a six-membered aromatic group, and
   R is an alkyl group having 1 to 10 carbon atoms, an aralkyl group having 7 to 9 carbon atoms or a $-(C_nH_{2n}O)_{\overline{m}}R'$ in which n is an integer of 2 to 5, m is an integer of 1 to 5, and R' is an alkyl group having 1 to 5 carbon atoms, in an amount of 0.01 to 5 weight % relative to polymerizable compound (a), and
   (c) at least one photo-polymerization initiator selected from benzoin alkyl ether base compounds expressed in terms of the following general formula (2):

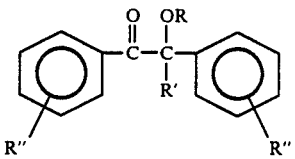

wherein
   R is an alkyl group,
   R' is selected from the group consisting of a hydrogen atom, and alkyl group, and a halogen atom, and
   R'' is one or more groups which may optionally be present on the respective rings of that formula, and are selected from the group consisting of an alkyl group, an alkoxy group, a halogen atom and an alkylamino group, in an amount of 0.01 to 5 weight % relative to polymerizable compound (a);
   (d) a reducing agent other than (c) in an amount of 0.01 to 5 weight % relative to polymerizable compound (a); and
   (e) a filler.

2. The composition as defined in claim 1, wherein said polymerizable compound containing at least one ethylenically unsaturated double-bond is a diacrylate and/or a dimethacrylate.

3. The composition as defined in claim 1 or 2, wherein said ketal base compound is any one of benzil dimethyl ketal, benzil diethyl ketal, benzil di(2-methoxyethyl)-ketal and 4,4'-dimethylbenzil-dimethyl ketal.

4. The composition as defined in claim 1, wherein said benzoin alkyl ether base compound is benzoin isobutyl ether.

5. The composition as defined in claim 1, wherein said reducing agent is any one of dimethylaminoethyl methacrylate, triethanolamine, 4-dimethylaminobenzoic acid methyl ester and 4-dimethylaminobenzoic acid ethyl ester.

* * * * *